(12) United States Patent
Brekner et al.

(10) Patent No.: US 6,169,052 B1
(45) Date of Patent: *Jan. 2, 2001

(54) METALLOCENE AND CATALYST USED FOR THE PREPARATION OF CHEMICALLY HOMOGENEOUS CYCLOOLEFIN COPOLYMERS

(75) Inventors: Michael-Joachim Brekner, Frankfurt am Main; Frank Osan, Kelkheim; Jürgen Rohrmann, Liederbach; Martin Antberg, Hofheim am Taunus, all of (DE)

(73) Assignee: Targor GmbH (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/840,255

(22) Filed: Apr. 14, 1997

Related U.S. Application Data

(63) Continuation of application No. 08/458,358, filed on Jun. 2, 1995, now abandoned, which is a continuation of application No. 08/219,786, filed on Mar. 30, 1994, now abandoned, which is a division of application No. 08/103,823, filed on Aug. 9, 1993, now Pat. No. 5,324,801, which is a continuation of application No. 07/846,668, filed on Mar. 5, 1992, now abandoned.

(30) Foreign Application Priority Data

Mar. 9, 1991 (DE) .................................................. 41 07 682

(51) Int. Cl.[7] ..................................................... B01J 31/00
(52) U.S. Cl. .......................... 502/152; 526/127; 526/160; 526/943; 556/11; 556/12; 556/13; 556/19; 556/20; 556/43; 556/51; 556/52; 556/53; 502/153
(58) Field of Search ................................. 556/11, 12, 13, 556/19, 20, 43, 51, 52, 53; 502/152, 153; 526/127, 160, 943

(56) References Cited

U.S. PATENT DOCUMENTS 3,268,627  8/1966  Emrick ................................... 260/897
3,305,538  2/1967  Natta et al. ........................... 260/93.7

(List continued on next page.)

FOREIGN PATENT DOCUMENTS 201 7192  11/1990  (CA) .
0 128 046  12/1984  (EP) .

(List continued on next page.)

OTHER PUBLICATIONS

Ewen et al., *J. Am. Chem. Soc.*, "Syndiospecific Propylene Polymerizations with Group 4 Metallo–cenes", vol. 110, pp. 6255–6256 (1988).

(List continued on next page.)

*Primary Examiner*—David W. Wu
*Assistant Examiner*—Ling-siu Choi
(74) *Attorney, Agent, or Firm*—Connolly Bove Lodge & Hutz LLP

(57) ABSTRACT

Chemically homogeneous cycloolefin copolymers of polycyclic olefins, such as, for example, norbornene or tetracyclododecene, with cycloolefins and/or acyclic olefins are obtained without ring opening and in a high space-time yield if a catalyst system is used which comprises an aluminoxane and a stereorigid metallocene compound of an element from groups IVb to VIb, of the formula

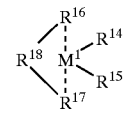

the part of the metallocene molecule formed by $M^1$ and the substituents $R^{16}$–$R^{17}$ having $C_1$-symmetry or being in the meso-form.

21 Claims, 2 Drawing Sheets

U.S. PATENT DOCUMENTS

| | | | |
|---|---|---|---|
| 3,364,190 | 1/1968 | Emrick | 260/93.7 |
| 4,178,424 | 12/1979 | Tenney | 526/283 |
| 4,261,880 | 4/1981 | Fujii et al. | 260/45.8 |
| 4,411,821 | 10/1983 | Howard, Jr. | 502/117 |
| 4,497,906 | 2/1985 | Hanji et al. | 502/110 |
| 4,530,914 | 7/1985 | Ewen et al. | 502/113 |
| 4,658,078 | 4/1987 | Slaugh et al. | 585/512 |
| 4,701,432 | 10/1987 | Welborn, Jr. | 502/113 |
| 4,794,096 | 12/1988 | Ewen | 502/117 |
| 4,797,162 | 1/1989 | Spietschka et al. | 106/498 |
| 4,849,487 | 7/1989 | Kaminsky et al. | 526/160 |
| 4,931,417 | 6/1990 | Miya et al. | 502/117 |
| 4,948,856 | 8/1990 | Minchak et al. | 526/281 |
| 5,003,019 | 3/1991 | Ishimaru et al. | 526/281 |
| 5,017,714 | 5/1991 | Welborn | 556/12 |
| 5,036,034 * | 7/1991 | Ewen | 502/117 |
| 5,086,134 * | 2/1992 | Antberg et al. | 526/126 |
| 5,087,677 * | 2/1992 | Brekner et al. | 526/160 |
| 5,093,483 | 3/1992 | Springer et al. | 534/642 |
| 5,162,278 | 11/1992 | Razavi | 502/152 |
| 5,176,941 | 1/1993 | Peuckert et al. | 427/226 |
| 5,416,228 * | 5/1995 | Ewen et al. | 556/7 |
| 5,436,305 | 7/1995 | Alt et al. | 526/160 |
| 5,451,649 | 9/1995 | Zenk et al. | 526/160 |

FOREIGN PATENT DOCUMENTS

| | | |
|---|---|---|
| 0 129 368 | 12/1984 | (EP) . |
| 0156464 | 2/1985 | (EP) . |
| 0203 799 | 5/1986 | (EP) . |
| 0 283 164 | 9/1988 | (EP) . |
| 316 155 | 11/1988 | (EP) . |
| 0 344 887 | 12/1989 | (EP) . |
| 0 351 392 | 1/1990 | (EP) . |
| 399 347 | 5/1990 | (EP) . |
| 61-221206 | 10/1986 | (JP) . |
| 87/00299 | 1/1987 | (WO) . |
| 87/03604 | 6/1987 | (WO) . |
| 90/5308 | 4/1991 | (ZA) . |

OTHER PUBLICATIONS

Ewen, *J. Am. Chem. Soc.*, "Mechanisms of Stereochemical-Control in Propylene Polymerizations with Soluble Group 4B Metallocene/Methylalumoxane Catalysts", vol. 106, pp. 6355–6364 (1984).

Ewen et al., *American Chemical Society*, "Crystal Structures and Stereospecific Propylene Polymerizations with Chiral Hafnium Metallocene Catalysts", vol. 109, pp. 6544–6545 (1987).

Buschermohle, Maria, Dissertation, "Experiments on the Sterio block polymerization of propylene with homogeneous Ziegler–Natta catalysts", Hamburg, Germany (1987).

Ewen et al., *Makromol. Chem. Makromol Symp.*, "Metallocene/Polypropylene Structural Relationships: Implications on Polymerization and StereochemicalControl Mechanisms", 48/49, pp. 253–295 (1991).

Klouras et al., *Monatshefte für Chemie*, "Ringsubstituierte [1]Titanocenophane", vol. 112, pp. 887–907 (1981).

Randall, *Journal of Polymer Science*, Polymer Physics Edition, "Carbon–13–Nuclear Magnetic Resonance Quantitative Measurements of Average Sequence Lengths fo Like Stereochemical Additions in Polypropylene and Polystyrene", vol. 14, pp. 2083–2094 (1976).

* cited by examiner

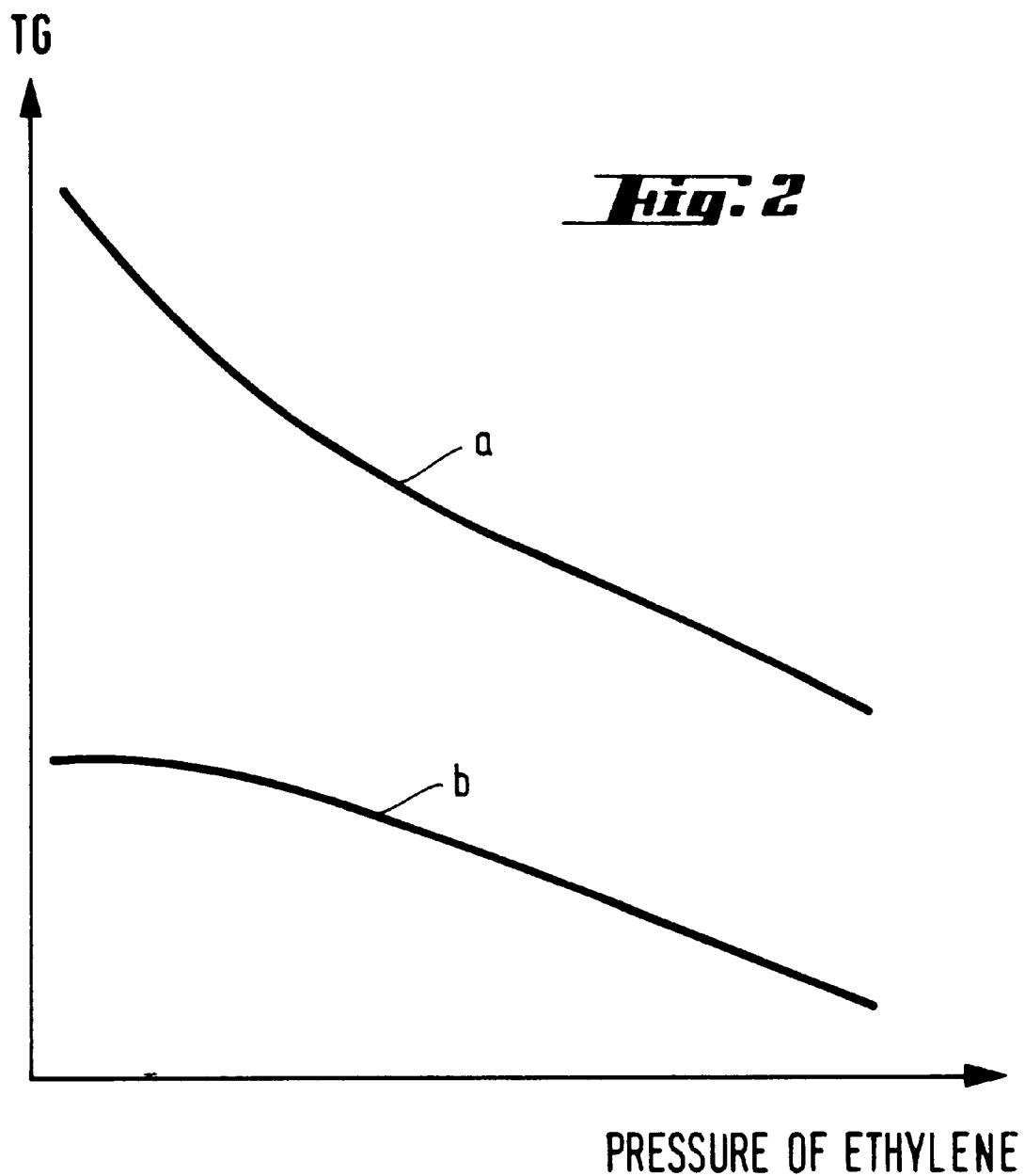

METALLOCENE AND CATALYST USED FOR THE PREPARATION OF CHEMICALLY HOMOGENEOUS CYCLOOLEFIN COPOLYMERS

This application is a continuation of Ser. No. 08/458,358, which was filed Jun. 2, 1995, now abandoned and which in turn is a continuation of Ser. No. 08/219,786 filed Mar. 30, 1994 and now abandoned, which is a divisional of Ser. No. 08/103,823 filed Aug. 9, 1993, which issued as U.S. Pat. No. 5,324,801, which is a continuation of Ser. No. 07/846,668 filed Mar. 5, 1992 and is now abandoned.

DESCRIPTION

The invention relates to a process for the preparation of copolymers of polycyclic olefins in which ring opening does not occur.

It is known that polycyclic olefins can be pulverized by means of various Ziegler catalysts. The polymerization proceeds, depending on the catalyst, via ring opening (cf. U.S. Pat. No. 4,178,424) or opening of the double bond (cf. EP-A 156 464, EP-A 283 164 and EP-A 203 799).

The disadvantage of ring-opening polymerization is that the polymer obtained contains double bonds, which can result in chain crosslinking and thus considerably restrict the processibility of the material by extrusion or injection molding.

Polymerization with opening of the double bond results, in the case of cyclic olefins, in a relatively slow polymerization rate (conversion rate).

A certain increase in the reaction rate has been achieved by using soluble metallocene compounds, such as bis(cyclopentadienyl)zirconium dichloride (cf. JP 61/221,206).

Catalysts which can be used for cyclic olefins are stereorigid chiral metallocene compounds, such as, for example, ethylenebis(indenyl)zirconium dichloride (cf. EP-A 283, 164) or dimethylsilylbis(indenyl)zirconium dichloride (cf. ZA 90/5308), the polymerization taking place with retention of the ring.

The glass transition temperatures of amorphous polymers correlate with the rates of incorporation of the comonomers into the polymer. For example, the glass transition temperature of norbornene-ethylene copolymers increases by from 4 to 5 Kelvin per mol percent of norbornene in the polymer. The glass transition temperature is an indirect measure of the heat resistance.

Experiments have shown that the incorporation ratios achieved when conventional metallocene catalysts are used are very sensitive to the reaction parameters such as monomer concentration, pressure and temperature.

In batchwise polymerization, the chemical homogeneity of the products is very conversion-dependent.

In continuous processes, a relatively long start-up period is necessary before steady-state reaction conditions are achieved. The chemically non-homogeneous products produced in this phase do not generally meet the specifications required for commercial products.

In both cases, low sensitivity of the catalysis to changes in the reaction parameters is desirable in order to save time and waste and to achieve higher space-time yields.

Random copolymers are characterized by a random distribution of the comonomers units in the polymer chain. This has the consequence of a relatively great fluctuation in the density of the material than in homopolymers or alternating copolymers. However, density fluctuations increase the proportion of scattered light and reduce the transparency. Applications in which, such as in optical fibers, extremely high demands are made on the optical transparency are thus restricted. Here too, chemically homogeneous products are therefore very desirable.

The term chemical homogeneity is taken to mean a virtually constant incorporation ratio of the monomers into the copolymer—via the respective polymer chain and via the total number of chains formed (over the polymerization time). Thus, the chemical homogeneity increases to the extent at which the structure of the copolymers approaches an alternating monomer sequence from a random sequence.

The object was therefore to find a process for the preparation of cycloolefin copolymers which, based on polymerization via the double bond, gives chemically homogeneous copolymers at a high space-time yield and in which, at the same time, changes in the reaction parameters have less effect on the chemical homogeneity of the products than in known processes.

It has been found that this object can be achieved by means of specific metallocene catalysts.

A BRIEF DESCRIPTION OF THE DRAWINGS

FIG. 2 shows the different course of a glass transition temperatures (Tg)/ethylene pressure curve.

Figure 1:
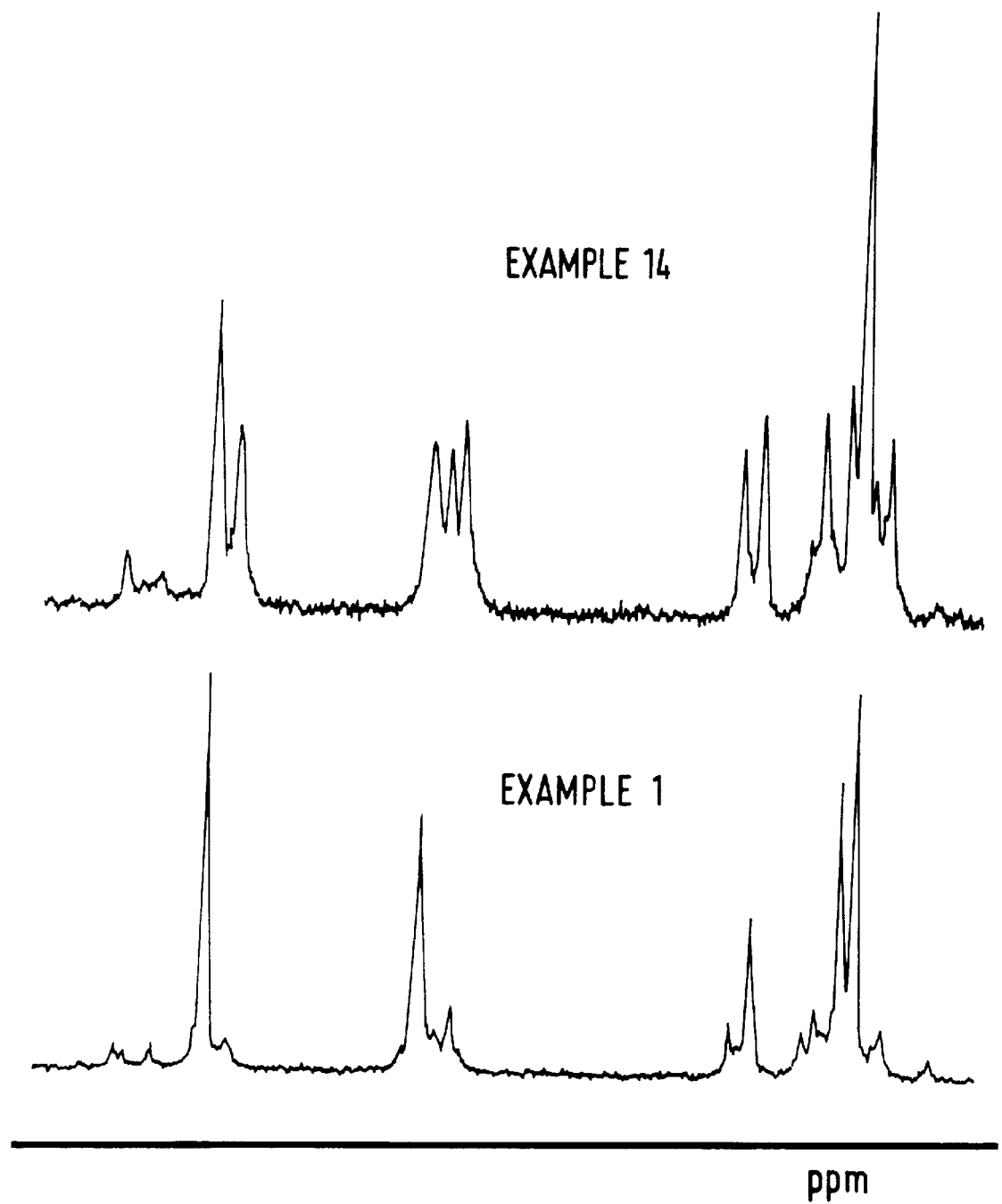
FIG. 1 shows the $^{13}$C-NMR spectra of the polymers obtained in accordance with Example 1.

The invention therefore relates to a process for the preparation of a cycloolefin copolymer by polymerization of from 0.1 to 99.9% by weight, based on the total amount of the monomers, of at least one monomer of the formula I, II, III, IV, V or VI

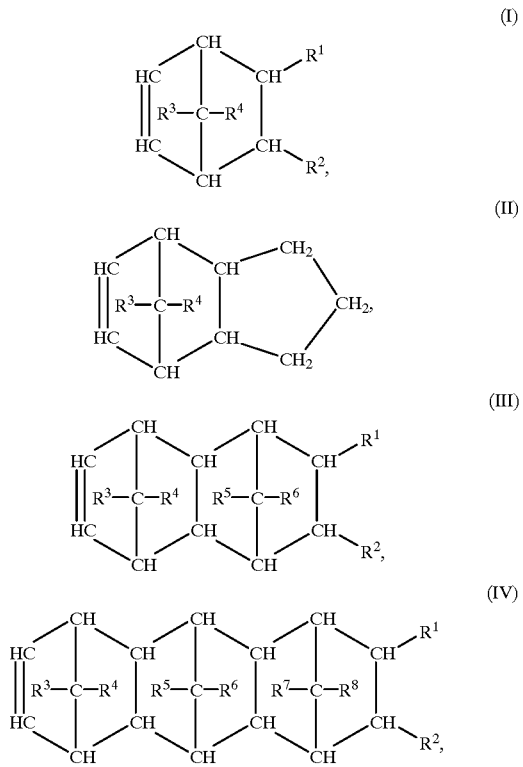

-continued (V)

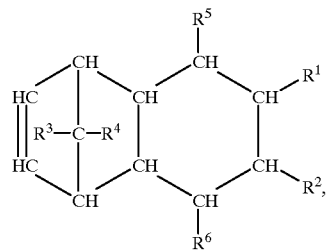

(VI)

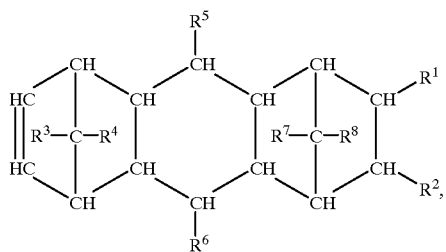

in which $R^1$, $R^2$, $R^3$, $R^4$, $R^5$, $R^6$, $R^7$ and $R^8$ are identical or different and are a hydrogen atom or a $C_6$–$C_{15}$-aryl or $C_1$–$C_8$-alkyl radical, it being possible for identical radicals in the different formulae to have different meanings, from 0 to 99.9% by weight, based on the total amount of the monomers, of a cycloolefin of the formula VII (VII)

in which n is a number from 2 to 10, and from 0 to 99.9% by weight, based on the total amount of the monomers, of at least one acyclic olefin of the formula VIII (VIII)

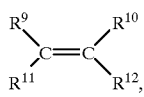

in which $R^9$, $R^{10}$, $R^{11}$ and $R^{12}$ are identical or different and are a hydrogen atom or a $C_1$–$C_8$-alkyl radical, at temperatures of from −78 to 150° C. and at a pressure of from 0.01 to 64 bar, in the presence of a catalyst which comprises an aluminoxane of the formula IX (IX)

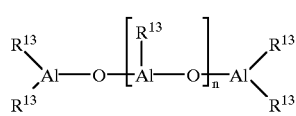

for the linear type and/or formula X (X)

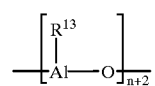

for the cyclic type, where, in the formulae IX and X, the radicals $R^{13}$ are identical or different and are a $C_1$–$C_6$-alkyl group or phenyl or benzyl, and n is an integer from 0 to 50, and a metallocene of the formula XI (XI)

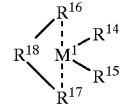

in which
$M^1$ is titanium, zirconium, hafnium, vanadium, niobium or tantalum,
$R^{14}$ and $R^{15}$ are identical or different and are a hydrogen atom, a halogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group,
$R^{16}$ and $R^{17}$ are identical or different and are a mononuclear or polynuclear hydrocarbon radical which is able to form a sandwich structure together with the central atom $M^1$,
$R^{18}$ is

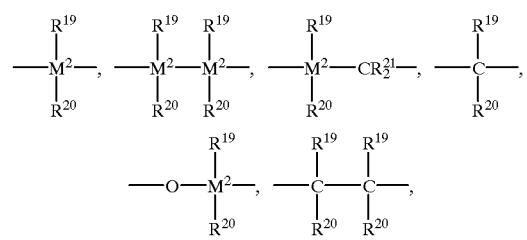

=$BR^{19}$, =$AlR^{19}$, —Ge—, —Sn—, —O—, —S—, =SO, =$SO_2$, =$NR^{19}$, =CO, =$PR^{19}$ or =$P(O)R^{19}$ where $R^{19}$, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{19}$ and $R^{20}$ or $R^{19}$ and $R^{21}$, in each case with the atoms connecting them, form a ring, and
$M^2$ is silicon, germanium or tin, wherein the part of the metallocene molecule formed by $M^1$ and the substituents $R^{16}$–$R^{17}$ has $C_1$ symmetry or, if $R^{16}$ and $R^{17}$ are identical, is in the meso-form.

Alkyl here in straight-chain or branched alkyl.
The monocyclic olefin VII may also be substituted (for example by aryl or alkyl radicals) for the purposes of the invention.
The polymerization is preferably carried out in the liquid cycloolefin monomer, in a cycloolefin monomer mixture or in concentrated solutions.

In the process according to the invention, at least one polycyclic olefin of the formula I, II, III, IV, V or VI, preferably a cycloolefin of the formula I or III, in which $R^1$, $R^2$, $R^3$, $R^4$, $R^5$, $R^6$, $R^7$ and $R^8$ are identical or different and are a hydrogen atom or a $C_1$–$C_8$-alkyl radical, it being possible for identical radicals in the different formulae to have different meanings, is polymerized. If desired, a monocyclic olefin of the formula VII in which n is a number from 2 to 10 is also used. Another comonomer is an acyclic olefin of the formula VIII in which $R^9$, $R^{10}$, $R^{11}$ and $R^2$ are identical or different and are a hydrogen atom or a $C_1$–$C_8$-alkyl radical. Ethylene and propylene are preferred.

In particular, copolymers of polycyclic olefins, preferably of the formula I or III, with the acyclic olefins VIII are prepared.

Particularly preferred cycloolefins are norbornene and tetracyclododecene, it being possible for these to be substituted by ($C_1$–$C_6$)-alkyl. They are preferably copolymerized with ethylene; ethylene-norbornene copolymers are of particular importance.

Preference is given to incorporation ratios of the comonomers VII and/or VIII into the copolymer of from 20:80 to 80:20. In particular, incorporation ratios of from 40:60 to 60:40 are preferred.

The polycyclic olefin (I to VI) is employed in an amount of from 0.1 to 99.9% by weight and the monocyclic olefin (VII) is employed in an amount of from 0.1 to 99.9% by weight, in each case based on the total amount of the monomers.

The concentration of the open-chain olefin is given by the solubility of the open-chain olefin in the reaction medium at the given pressure and the given temperature.

Polycyclic olefins, monocyclic olefins and open-chain olefins are also taken to mean mixtures of two or more olefins of the particular type. This means that, in addition to polycyclic bicopolymers, it is also possible to prepare ter- and multicopolymers by the process according to the invention. Copolymers of the cycloolefins VII with the acyclic olefins VIII can also advantageously be obtained by the process described. Of the cycloolefins VII, cyclopentene, which may be substituted, is preferred.

The catalyst to be used for the process according to the invention comprises an aluminoxane and at least one metallocene (transition-metal component) of the formula XI

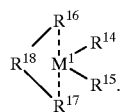

(XI)

In the formula XI, $M^1$ is a metal from the group comprising titanium, zirconium, hafnium, vanadium, niobium and tantalum, preferably zirconium and hafnium. Zirconium is particularly preferred.

$R^{14}$ and $R^{15}$ are identical or different and are a hydrogen atom, a $C_1$–$C_{10}$—, preferably $C_1$–$C_3$-alkyl group, a $C_1$–$C_{10}$—, preferably $C_1$–$C_3$-alkoxy group, a $C_6$–$C_{10}$—, preferably $C_6$–$C_8$-aryl group, a $C_6$–$C_{10}$—, preferably $C_6$–$C_8$-aryloxy group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, or a halogen atom, preferably chloride.

$R^{16}$ is preferably fluorenyl and $R^{17}$ is preferably cyclopentadienyl, it being possible for these radicals to be substituted (in the case of $C_1$ symmetry), or the two radicals are identical and are (substituted) indenyl or substituted cyclopentadienyl (meso-form).

$R^{18}$ is a single- or multi-membered bridge which links the radicals $R^{16}$ and $R^{17}$ and in preferably

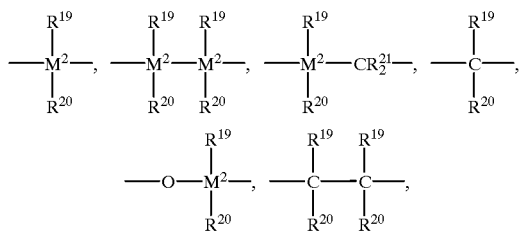

$=BR^{19}$, $=AlR^{19}$, —Ge—, —Sn—, —O—, —S—, $=SO$, $=SO_2$, $=NR^{19}$, $=CO$, $=PR^{19}$ or $=P(O)R^{19}$ where $R^{19}$, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^{19}$ and $R^{20}$ or $R^{19}$ and $R^{21}$, in each case together with the atoms connecting them, form a ring.

$R^{18}$ is preferably a

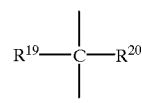

radical and particularly preferably

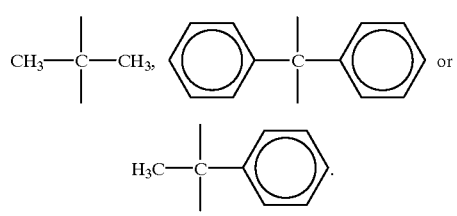

of the radicals $R^{19}$—$M^2$—$R^{20}$, dimethylsilyl is particularly important.

$M^2$ is silicon, germanium or tin, preferably silicon or germanium.

The bridged metallocenes can be prepared in accordance with the known reaction scheme below:

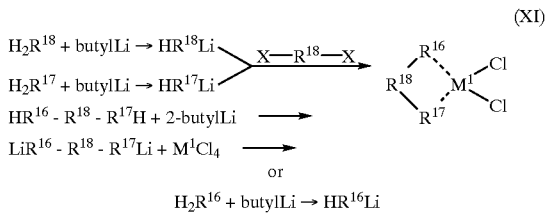

(XI)

-continued

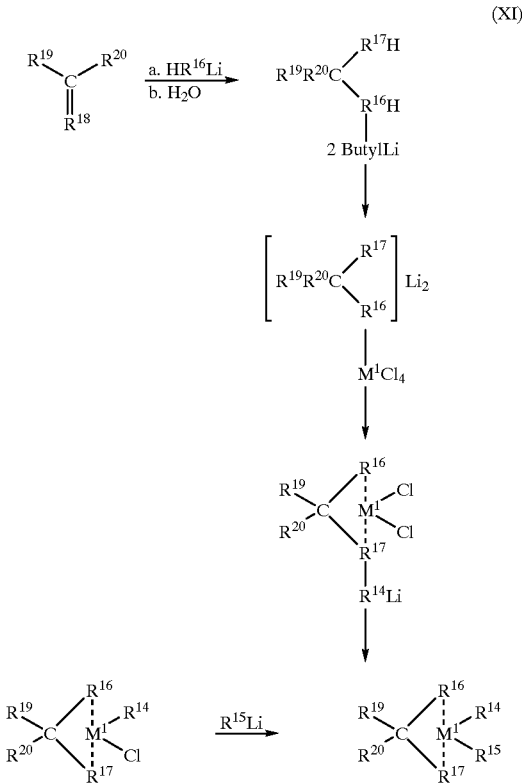

(XI)

The above reaction scheme also applies to the case where $R^{19}=R^{20}$ and/or $R^{14}=R^{15}$ (cf. Journal of Organometallic Chem. 288 (1985) 63–67 and EP-A 320 762).

Of the metallocenes XI according to the invention which have $C_1$ symmetry in the part of the molecule formed by the central atom $M^1$ and the substituents $R^{16}$–$R^{17}$ (i.e. this moiety contains no higher symmetry elements and can only be superimposed on itself by rotation through 360°- one-fold axis), the following should be mentioned in particular:

isopropylene(9-fluorenyl)(1-(3-isopropyl) cyclopentadienyl)zirconium dichloride, isopropylene (9-fluorenyl)(1-(3-methyl)cyclopentadienyl)zirconium dichloride, diphenylmethylene(9-fluorenyl)(1-(3-methyl)cyclopentadienyl)zirconium dichloride, methylphenylmethylene(9-fluorenyl)(1-(3-methyl) cyclopentadienyl)zirconium dichloride, dimethylsilyl (9-fluorenyl)(1-(3-methyl)cyclopentadienyl)zirconium dichloride, diphenylsilyl(9-fluorenyl)(1-(3-methyl) cyclopentadienyl)zirconium dichloride, diphenylmethylene(9-fluorenyl)(1-(3-tert.-butyl) cyclopentadienyl)zirconium dichloride and isopropylene(9-fluorenyl)(1-(3-tert.-butyl) cyclopentadienyl)zirconium dichloride and the corresponding hafnium dichlorides.

For the importance of the term $C_1$ symmetry, cf. K. Mislow "Einführung in die Stereochemie" [Introduction to Stereochemistry], Verlag Chemie, 1st Edition 1967, pp. 23 ff.

Of the metallocenes whose moiety $M^1$, $R^{16}$, $R^{17}$ is in the meso-form, the following should be mentioned in particular:
meso-dimethylsilylbis(1-(3-methyl)cyclopentadienyl) zirconium dichloride, meso-dimethylsilylbis(1-(2,4-dimethyl)cyclopentadienyl)zirconium dichloride, meso-dimethylsilylbis(1-indenyl)zirconium dichloride, meso-diphenylsilylbis(1-indenyl)zirconium dichloride, meso-isopropylenebis(1-indenyl)zirconium dichloride, meso-diphenylmethylenebis(1-indenyl)zirconium dichloride, meso-methylphenylmethylenebis(1-indenyl)zirconium dichloride, meso-diphenylsilylbis (1-indenyl)hafnium dichloride, meso-dimethylsilylbis (1-indenyl)hafnium dichloride, meso-1,2-ethylenebis (1-indenyl)zirconium dichloride and meso-1,2-ethylenebis(1-indenyl)hafnium dichloride.

For the purposes of the present invention, meso-form means that the substituents $R^{16}$ and $R^{17}$ can be converted into one another through a mirror plane between $R^{16}$ and $R^{17}$ which passes through the central atom $M^1$ (cf. K. Mislow, "Einf. in die Stereochemie" [Introduction to Stereochemistry], p. 83).

Preference is generally given to ligand systems ($R^{16}$–$R^{18}$) which are able to exert a different steric interaction on the ligands $R^{14}$ and $R^{15}$. The nature of the ligands $R^{14}$ and $R^{15}$ is unimportant.

The cocatalyst is (preferably) an aluminoxane of the formula IX and/or of the formula X. In these formulae, the radicals $R^{13}$ may be identical or different and are a $C_1$–$C_6$-alkyl group, preferably methyl, ethyl, isobutyl, butyl or neopentyl, or phenyl or benzyl. Methyl is particularly preferred. n is an integer from 0 to 50, preferably from 5 to 40.

The aluminoxane can be prepared in various ways by known processes. One of the methods is, for example, to react an aluminum hydrocarbon compound and/or a hydridoaluminum hydrocarbon compound with water (gaseous, solid, liquid or bonded—for example as water of crystallization) in an inert solvent (such as, for example, toluene). To prepare an aluminoxane containing different alkyl groups $R^{13}$, two different trialkylaluminum compounds ($AlR_3+AlR'_3$), in accordance with the desired composition, are reacted with water (cf. S. Pasynkiewicz, Polyhedron 9 (1990) 429 and EP-A 302 424).

The precise structure of the aluminoxanes is not known.

Irrespective of the preparation method, all the aluminoxane solutions have in common a varying content of unreacted aluminum starting compound, which is in free form or as an adduct.

It is possible to preactivate the metallocene using an aluminoxane of the formula (IX) and/or (X) before use in the polymerization reaction. This significantly increases the polymerization activity.

The preactivation of the transition-metal compound is carried out in solution. A preferred method here is to dissolve the metallocene in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight to the saturation limit, preferably from 5 to 30% by weight, in each case based on the total solution. The metallocene can be employed in the same concentration, but is preferably employed in an amount of from $10^{-4}$ to 1 mol per mol of aluminoxane. The preactivation time is from 5 minutes to 60 hours, preferably from 5 to 60 minutes. The reaction is carried out at a temperature of from −78C to 100° C., preferably from 0 to 70° C.

The metallocene may also be prepolymerized or applied to a support. Prepolymerization is preferably carried out using the (or one of the) olefin(s) employed in the polymerization.

Examples of suitable supports are silica gels, aluminum oxides, solid aluminoxane or other inorganic support materials. Another suitable support material is a polyolefin powder in finely divided form.

A further possible embodiment of the process according to the invention comprises using a salt-like compound of the formula $R_xNH_{4-x}BR'_4$ or of the formula $R_3PHBR'_4$ as cocatalyst instead of or in addition to an aluminoxane. In these formulae, X is 1, 2 or 3, R is identical or different alkyl or aryl, and R' is aryl, which may also be fluorinated or partially fluorinated. In this case, the catalyst comprises the product of the reaction of a metallocene with one of said compounds (cf. EP-A 277 004).

Any solvent added to the reaction mixture is a conventional inert solvent, such as, for example, an aliphatic or cycloaliphatic hydrocarbon, a gasoline or hydrogenated diesel oil fraction or toluene.

The metallocene compound is used in a concentration, based on the transition metal, of from $10^{-3}$ to $10^{-8}$, preferably from $10^{-4}$ to $10^{-7}$, mol of transition metal per $dm^3$ of reactor volume. The aluminoxane is used in the concentration of from $10^{-4}$ to $10^{-1}$, preferably from $10^{-4}$ to $2.10^{-2}$, mol per $dm^3$ of reactor volume, based on the aluminum content. In principle, however, higher concentrations are also possible.

In the preparation of copolymers, the variation of the molar ratios between the polycyclic olefin and the open-chain olefin employed can occur in a broad range. Preference is given to molar ratios (cycloolefin:open-chain olefin) of 3:1 to 100:1. The incorporation rate of comonomers can be controlled virtually as desired through the choice of polymerization temperature, through the concentration of the catalyst components and the molar ratio employed or the pressure of the gaseous, open-chain olefin. Preferred incorporation rates are 20 to 80 mol % of the cyclic components, and particularly preferred incorporation rates are from 40 to 60 mol % of the cyclic components.

The mean molecular weight of the copolymer formed can be controlled in a known manner through the metering of hydrogen, by varying the catalyst concentration or by varying the temperature.

The polydispersity $M_w/M_n$ of the copolymers, at values of 2.0–3.5, is extremely narrow. This results in a property profile of the polymers which makes them particularly suitable for injection molding.

Furthermore, it has been observed from NMR spectra that these cycloolefin copolymers also differ significantly in microstructure from those prepared using conventional metallocene catalysts (cf. FIG. 1). A possible explanation of this difference is that the catalysts according to the invention polymerize alternately due to their specific symmetry. In accordance with the current knowledge, it must be assumed that the cycloolefin copolymers according to the invention contain alternating cycloolefin sequences which enable a structural differentiation to be made by NMR (cf. FIG. 1).

The materials prepared according to the invention are particularly suitable for the production of extruded parts, such as films, tubes, pipes, rods and fibers, and for the production of injection-molded articles of any desired shape and size.

An important property of the materials according to the invention is their transparency. Optical applications of the extruded or injection-molded parts made from these materials therefore have particularly great importance. The refractive index, determined using an Abbe refractometer and mixed light, of the reaction products described in the examples below is in the range from 1.520 to 1.555. Since the refractive index is very close to that of crown glass (n=1.51), the products according to the invention can be used as a glass substitute for various applications, such as, for example, lenses, prisms, support plates and films for optical data carriers, for video disks, for compact disks, as cover and focusing screens for solar cells, as cover and diffuser screens for high-performance objects, and as optical waveguides in the form of fibers or films.

The polymers according to the invention can also be employed for the preparation of polymer alloys. The alloys can be prepared in the melt or in solution. The alloys each have a property combination of the components which is favorable for certain applications. The following polymers can be employed for alloys with the polymers according to the invention:

polyethylene, polypropylene, (ethylene-propylene) copolymers, polybutylene, poly(4-methyl-1-pentene), polyisoprene, polyisobutylene, natural rubber, poly(methyl methacrylate), further polymethacrylates, polyacrylates, (acrylate-methacrylate) copolymers, polystyrene (styreneacrylonitrile) copolymers, bisphenol A polycarbonate, further polycarbonates, aromatic polyester carbonates, polyethylene terephthalate, polybutylene terephthalate, amorphous polyacrylates, nylon 6, nylon 66, further polyamides, polyaramids, polyether ketones, polyoxymethylene, polyoxyethylene, polyurethanes, polysulfones, polyether sulfones and polyvinylidene fluoride.

The glass transition temperatures (Tg) indicated in the examples below were determined by DSC (differential scanning calorimetry) at a heating rate of 20° C./min. The viscosities indicated were determined in accordance with DIN 53 728.

EXAMPLE 1

A 1.5 $dm^3$ reactor was filled with ethylene and filled with 600 $cm^3$ of an 85 percent by weight solution of norbornene in toluene. The solution was saturated with ethylene by repeatedly injecting ethylene (6 bar). A pressure of 0.5 bar (overpressure) was set, 5 $cm^3$ of a toluene solution of methylaluminoxane (10.1% by weight of methylaluminoxane having a molecular weight of 1,300 g/mol, determined cryoscopically) were introduced into the reactor, and the mixture was stirred at 70° C. for 15 minutes. A solution of 10 mg of isopropylene(9-fluorenyl)(1-(3-methyl) cyclopentadienyl)zirconium dichloride in 5 $cm^3$ of a toluene solution of methylaluminoxane was added after preactivation for 15 minutes. (In order to regulate the molecular weight, hydrogen can be added before addition of the catalyst).

The mixture was polymerized at 70° C. for one hour with stirring (750 rpm), the ethylene pressure being kept at 0.5 bar by reintroduction.

The reaction solution was discharged into a vessel and rapidly added dropwise to 5 $dm^3$ of acetone, and the mixture was stirred for 10 min and subsequently filtered.

The solid obtained was washed a number of times alternately with 10% strength hydrochloric acid and acetone. It was washed until neutral and again stirred with acetone. The re-filtered polymer was dried for 15 hours at 80° C. and at a pressure of 0.2 bar.

18 g of a colorless polymer were obtained. A viscosity of 32 $cm^3$/g and a glass transition temperature (Tg) of 145° C. were measured. The norbornene/ethylene incorporation ratio, according to the NMR spectrum, is about 50 mol % of norbornene to 50 mol % of ethylene.

EXAMPLES 2 TO 6

The polymerization was carried out analogously to Example 1, the ethylene overpressures being varied in accordance with Table 1.

TABLE 1

| Ex. No. | Amount of catalyst (mg) | Ethylene over-pressure (bar) | Reaction time (min) | Yield (g) | Viscosity (cm³/g) | Tg (° C.) |
|---|---|---|---|---|---|---|
| 1 | 10 | 0.5 | 15 | 18 | 32 | 145 |
| 2 | 11 | 1 | 60 | 11 | 47 | 146 |
| 3 | 10 | 2 | 15 | 44 | 55 | 140 |
| 4 | 5 | 4 | 15 | 50 | 79* | 132 |
| 5 | 10 | 6 | 30 | 29 | 96* | 120 |
| 6 | 0.7 | 10 | 45 | 10 | 144 | 93 |

*measured in o-dichlorobenzene

EXAMPLES 7 TO 9

The polymerizations were carried out analogously to Example 1, with some conditions, summarized in Table 2, being changed.

TABLE 2

| Ex. No. | Amount of catalyst (mg) | Ethylene over-pressure (bar) | Reaction time (min) | Reaction temperature (° C.) | Yield (g) | Tg (° C.) |
|---|---|---|---|---|---|---|
| 7 | 61 | 0.5 | 60 | 40 | 7 | 144 |
| 8 | 61 | 1 | 60 | 40 | 9 | 133 |
| 9 | 120 | 0 | 30 | 25 | 17 | 139 |

COMPARATIVE EXAMPLES 10 TO 16

The polymerizations were carried out analogously to Example 1. The metallocene employed was isopropylene(9-fluorenyl)(cyclopentadienyl)zirconium dichloride. This metallocene does not meet the requirements according to the invention for symmetry in the moiety formed by $M^1$ and $R^{16}$–$R^{17}$, since further symmetry elements, such as, for example, vertical mirror planes, occur here. The reaction conditions shown in Table 3 were chosen.

TABLE 3

| Ex. No. | Amount of metallocene (mg) | Ethylene over-pressure (bar) | Reaction time (min) | Yield (g) | Viscosity (cm³/g) | Tg (° C.) |
|---|---|---|---|---|---|---|
| 10 | 1 | 0.5 | 60 | 44 | 110 | 200 |
| 11 | 1 | 1 | 60 | 39 | 93 | 192 |
| 12 | 0.5 | 2 | 60 | 29 | 117 | 180 |
| 13 | 10 | 3 | 60 | 21 | 132 | 162 |
| 14 | 1 | 6 | 15 | 43 | 130 | 153 |
| 15 | 2 | 6 | 10 | 29 | 124 | 151 |
| 16 | 10 | 10 | 30 | 22 | 118 | 119 |

EXAMPLE 19

The polymerization was carried out as in Example 1. An 85 percent by weight solution of tetracyclododecene in toluene was employed, and the polymerization was carried out for one hour at 70° C. with an ethylene overpressure of 10 bar and with 1 mg of isopropylene(9-fluorenyl)(1-(3-methyl)cyclopentadienyl)zirconium dichloride.

3.2 g of copolymer were obtained. The glass transition temperature was 159° C.

EXAMPLE 20

The norbornene solution was replaced by liquid norbornene and the polymerization was carried out at an ethylene pressure of 0.5 bar with 10 mg of meso-dimethylsilylbis(1-(2,4-dimethyl)cyclopentadienyl)zirconium dichloride. 5.6 g of copolymer were obtained. The glass transition temperature was 102° C.

EXAMPLE 21

Plates (diameter 6 cm) were pressed at 300° C. in a film press from in each case 3 g of each of the polymers obtained in accordance with Examples 1 to 6. The plates were subsequently immediately quenched in cold water. Samples of these pressed plates were reexamined by DSC. The glass transition temperatures (Tg), recrystallization temperatures (Ter) and melting points (TM) found on the first heating are shown in Table 4.

TABLE 4

| Polymer from Example | Tg/° C. | Ter/° C. | Tm/° C. |
|---|---|---|---|
| 1 | 143 | — | 244 |
| 2 | 140 | 214 | 258 |
| 3 | 136 | 216 | 271 |
| 4 | 130 | 226 | 276 |
| 5 | 118 | 211 | 264 |
| 6 | 108 | 167 | 235 |

EXAMPLE 22

The polymerization was carried out analogously to Example 1. An 85% strength by weight solution of tetracyclododecene in toluene was employed and the polymerization was carried out for one hour at 70° C. and an ethylene pressure (overpressure) of 1 bar and with 10 mg of methylphenylmethylene (9-fluorenyl)[1-(3-methyl)cyclopentadienyl]zirconium dichloride. 18.2 g of copolymer were obtained. A sample was melted at 350° C. under nitrogen and subsequently quenched. A glass transition temperature of 192° C., a crystallization temperature of 253° C. and a melting point of 335° C. were measured.

EXAMPLE 23

The polymerization was carried out analogously to Example 1. 500 cm³ of 5-methylnorborn-2-ene were employed and the polymerization was carried out for two hours at 70° C. and an ethylene pressure (overpressure) of 4 bar with 2 mg of isopropenyl(9-fluorenyl)[1-(3-methyl)cyclopentadienyl]zirconium dichloride and 60 ml of methylaluminoxane. 21.3 g of polymer were obtained. The solution viscosity was 104 cm³/g and the glass transition temperature was 117° C. It was not possible to find any crystallization or melting point in the DSC. According to $^{13}$C-NMR, 41 molt % of 5-methylnorbornene are present in the copolymer.

EXAMPLE 24

The polymerization was carried out analogously to Example 1. 12 mg of isopropenyl(9-fluorenyl)-[1-(3-isopropyl)cyclopentadienyl]zirconium dichloride were employed and the polymerization was carried out for one hour at 40° C. and an ethylene overpressure of 3 bar. 17.9 g of polymer were obtained. The melting point was 286° C.

EXAMPLE 25

The polymerization was carried out analogously to Example 5. 5 mg of diphenylmethylene(9-fluorenyl)[1-(3-methyl)cyclopentadienyl]zirconium dichloride were employed. 43 g of polymer were obtained. The glass transition temperature was 124° C. and the melting point was 275° C.

Key to the Figures:

FIG. 1 shows the $^{13}$C-NMR spectra of the polymers obtained in accordance with Example 1 (metallocene catalyst according to the invention having $C_1$-symmetry in the part of the metallocene molecule formed by $M^1$ and $R^{16}$–$R^{17}$) and Example 14 (conventional metallocene catalyst; cf. the explanation of Comparative Examples 10 to 16). The differences in microstructure are clearly visible.

FIG. 2 shows the different course of the glass transition temperature (Tg)/ethylene pressure curve on use of a) conventional metallocene catalysts without a $C_1$ symmetry or,with no meso-form in said moiety of the metallocene (upper curve, plotted using the data from Table 3) and b) on use of metallocene catalysts according to the invention (lower curve, plotted using the data from Table 1).

In addition to the very different curve shapes, the much lower dependence of the glass transition temperature (Tg) of the copolymer obtained on the ethylene pressure (change in the reaction parameters) when metallocene catalysts according to the invention are used should be particularly emphasized. This smaller effect of the reaction parameters on the reaction product inevitably results in chemically homogeneous copolymers.

What is claimed is:

1. A compound (metallocene) of The formula XI

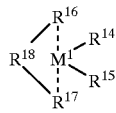

(XI)

in which $M^1$ is titanium, zirconium, hafnium, vanadium, niobium or tantalum, $R^{14}$ and $R^{15}$ are identical or different and are a hydrogen atom, a halogen atom, a $C_1$–$C_{10}$-alkyl group, a $C_1$–$C_{10}$-alkoxy group, a $C_8$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, $R^{16}$ and $R^{17}$ are different and are a fluorenyl ligand and a substituted cyclopentadienyl ligand, $R^{18}$

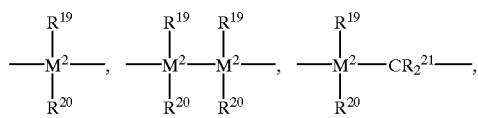

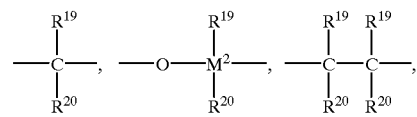

=BR$^{19}$, =AlR$^{19}$, =NR$^{19}$, =PR$^{19}$ or =P(O)R$^{19}$ wherein $R^{19}$ is a $C_6$–$C_{10}$-aryl group, $R^{20}$ and $R^{21}$ are identical or different and are a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_6$–$C_{40}$-arylalkenyl group or a $C_7$–$C_{40}$-alkylaryl group, or $R^{19}$ and $R^{20}$ or $R^{19}$ and $R^{21}$, in each case with the atoms connecting them, form a ring, and $M^2$ is silicon, germanium or tin and the metallocene has a $C_1$ symmetry in the part of the metallocene formed by $M^1$ and $R^{16}$ and $R^{17}$.

2. The compound as claimed in claim 1, wherein $M^1$ is zirconium or hafnium.

3. The compound as claimed in claim 1, wherein $R^{14}$ and $R^{15}$ are identical or different and are a halogen atom or a $C_1$–$C_{10}$-alkyl group and $M^2$ is silicon.

4. The compound as claimed in claim 3, wherein $R^{14}$ and $R^{15}$ are a chlorine atom and $M^1$ is zirconium.

5. The compound as claimed in claim 1, wherein $R^{18}$ is

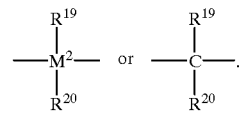

6. The compound as claimed in claim 5, wherein $M^2$ is silicon, $M^1$ is zirconium or hafnium, $R^{14}$ and $R^{15}$ are identical or different and are a $C_1$–$C_3$-alkyl or a halogen atom and $R^{20}$ is hydrogen, a $C_1$–$C_{10}$-alkyl group, a $C_1$–$C_{10}$-fluoroalkyl group, a $C_6$–$C_{10}$-fluoroaryl group or a $C_6$–$C_{10}$-aryl group.

7. The compound as claimed in claim 6, wherein $R^{19}$ is a $C_6$-aryl group.

8. The compound as claimed in claim 4, wherein $R^{19}$ is a $C_6$-aryl group.

9. The compound as claimed in claim 7, wherein $R^{20}$ is a $C_1$–$C_{10}$-alkyl or a $C_6$–$C_{10}$-aryl.

10. The compound as claimed in claim 9, wherein $R^{20}$ is a $C_1$-alkyl or a $C_6$-aryl.

11. The compound as claimed in claim 10, wherein the metallocene is diphenylmethylene(9-fluorenyl)(1-(3-methyl)cyclopentadienyl)$M^1Cl_2$, methylphenylmethylene (9-fluorenyl)(1-(3-methyl)cyclopentadienyl)$M^1Cl_2$, diphenylsilyl(9-fluorenyl)(1-(3-methyl)cyclopentadienyl) $M^1Cl_2$, diphenylmethylene(9-fluorenyl)(1-(3-tert.butyl) cyclopentadienyl)$M^1Cl_2$ wherein $M^1$ is zirconium or hafnium.

12. A catalyst which comprises the combination which comprises an aluminoxane of the formula IX

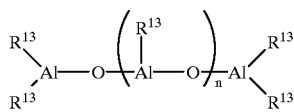

(IX)

for the linear type and/or formula X

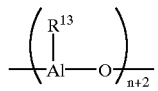

(X)

for the cyclic type, wherein $R^{13}$ are identical or different and are a $(C_1-C_5)$-alkyl group, phenyl or benzyl, and n is an integer from 0 to 50, combined with the metallocene as claimed in claim 1.

13. The catalyst as claimed in claim 12, wherein the metallocene is diphenylmethylene(9-fluorenyl)(1-(3-methyl)cyclopentadienyl)$M^1Cl_2$, methylphenylmethylene(9-fluorenyl)(1-(3-methyl)cyclopentadienyl)$M^1Cl_2$, diphenylsilyl(9-fluorenyl)(1-(3-methyl)cyclopentadienyl)$M^1Cl_2$, diphenylmethylene(9fluorenyl)(1-(3-tert-butyl)cyclopentadienyl)$M^1Cl_2$, wherein $M^1$ is zirconium or hafnium.

14. The catalyst as claimed in claim 12, wherein said aluminoxane is methylaluminoxane.

15. The catalyst as claimed in claim 12, wherein $R^{18}$ is

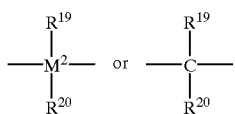

$M^2$ is silicon, $M^1$ is zirconium or hafnium, $R^{14}$ and $R^{15}$ are identical or different and are a $C_1-C_3$-alkyl or a halogen atom and $R^{20}$ is hydrogen, a $C_1-C_{10}$-alkyl group, a $C_1-C_{10}$-fluoroalkyl group, a $C_6-C_{10}$-fluoroaryl group or a $C_6-C_{10}$-aryl group.

16. The catalyst as claimed in claim 15, wherein $R^{19}$ is a $C_6$-aryl group.

17. The catalyst as claimed in claim 16, wherein $R^{20}$ is a $C_1-C_{10}$-alkyl or a $C_6-C_{10}$-aryl.

18. The catalyst as claimed in claim 17, wherein $R^{20}$ is a $C_1$-alkyl or a $C_6$-aryl and said aluminoxane is methylaluminoxane.

19. Isopropylene(9-fluorenyl)(1-(3-isopropyl)cyclopentadienyl)$M^1Cl_2$ therein $M^1$ is zirconium or hafnium.

20. A catalyst which comprises the combination which comprises an aluminoxane of the formula IX

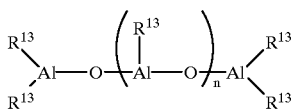

(IX)

for the linear type and/or formula X

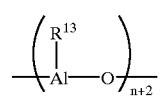

(X)

for the cyclic type, wherein $R^{13}$ are identical or different and-are a $(C_1-C_2)$-alkyl group, phenyl or benzyl, and n is an integer from 0 to 50, combined with the metallocene as claimed in claim 19.

21. The catalyst as claimed in claim 20, wherein said aluminoxane is methylaluminoxane.

* * * * *